United States Patent [19]

Rubin et al.

[11] 4,191,234
[45] Mar. 4, 1980

[54] COVER FOR ROTATABLE SAMPLE TRAY

[75] Inventors: Laurence A. Rubin, Columbia; William S. Baker, Annapolis, both of Md.

[73] Assignee: Baxter Travenol Laboratories, Inc., Deerfield, Ill.

[21] Appl. No.: 935,544

[22] Filed: Aug. 21, 1978

[51] Int. Cl.² .............................................. B67C 3/26
[52] U.S. Cl. .................................. 150/52 R; 141/130; 206/303
[58] Field of Search ............... 206/303, 427, 429, 562, 206/563; 150/52 R; 141/130

[56] References Cited

U.S. PATENT DOCUMENTS

| | | | |
|---|---|---|---|
| 2,604,249 | 7/1952 | Gorham | 141/130 |
| 2,997,077 | 8/1961 | Rodrigues | 141/130 |
| 3,605,435 | 12/1969 | Taylor | 206/427 X |
| 4,131,426 | 12/1978 | Range | 141/130 X |

*Primary Examiner*—Donald F. Norton
*Attorney, Agent, or Firm*—Henry W. Collins; Paul Flattery; Thomas Vigil

[57] ABSTRACT

The cover is made from a sheet of transparent plastic material and has a generally annular shape, i.e., the general shape of a flat ring, which is easily received over an annular rotatable sample tray having a plurality of sample cups therein. The cover has a horizontally radially extending projection adapted to engage a post on a table top supporting the sample tray to prevent rotation of the cover and an annular shoulder on the underside of the cover which fits around a circular envelope defined by the radially outwardly disposed top side edges of the sample cups in the sample tray and which engages the top side edges of the sample cups to prevent horizontal movement of the cover as the tops of the sample cups frictionally engage the underside of the cover and exert a moment force on the cover when the sample tray is rotated. The cover also has an opening therethrough for allowing liquid sample to be inserted or withdrawn from a sample cup when such sample cup is in registry with the opening.

14 Claims, 6 Drawing Figures

COVER FOR ROTATABLE SAMPLE TRAY

BACKGROUND OF THE INVENTION

1. Field of the Invention

The field of the invention is automatic sample and reagent transfer and dispensing devices utilized with a centrifugal chemical analysis apparatus. More specifically, the invention relates to a cover for a sample tray which is utilized with the transfer and dispensing device wherein a liquid sample, such as blood plasma, is transferred from a sample cup to a chamber or well in a transfer disc which, when filled, is placed in the centrifugal chemical analysis apparatus for making a particular chemical analysis of the sample.

2. Description of the Prior Art

Centrifugal chemical analysis apparatus presently utilize a transfer disc having a plurality of channels arranged in a spoke-like configuration therein, each channel including at least three wells or chambers, one for receiving reagent, one for receiving sample and an outer well or chamber in which the sample and reagent are mixed during rotation of the transfer disc and then transferred to a reaction chamber where light is periodically passed through the reaction chamber to monitor the absorbance of the mixture each time a centrifuge device mounting the transfer disc rotates past a fixed position in the centrifugal chemical analysis apparatus.

In the use of the centrifugal chemical analysis apparatus it is first necessary to fill the reagent chambers with reagent and the sample chambers with different samples, such as blood plasma obtained from different patients. This is accomplished by placing the transfer disc and an annular sample tray on a turntable mounted on the table top of an automatic sample and reagent transfer and dispensing device.

The centrifugal chemical analysis apparatus can be of the type sold under the trademark ROTOCHEM by American Instrument Company, a division of Baxter Travenol Laboratories, Inc., of Silver Spring, Md., and the automatic sample and reagent transfer and dispensing device can be of the type sold under the trademark ROTOFILL by American Instrument Company, a division of Baxter Travenol Laboratories, Inc., of Silver Spring, Md.

The rotatable sample tray has an annular configuration with a plurality of sample cups mounted therein. The transfer disc and the sample tray are mounted on a turntable on the table top of the transfer and dispensing device on which are also disposed two arms extending respectively from two posts on the table top of the transfer and dispensing device and having aspirating or dispensing dip tubes at the outer ends thereof.

In the use of the transfer and dispensing device, the sample tray and transfer disc are indexed to rotate a sample cup to a sample pickup position, and the transfer disc to a reagent dispensing position, where a dip tube will pick up a given amount of sample, such as blood plasma, from a sample cup and then dispense that given amount of sample into a selected sample receiving well. At the same time a given amount of a selected reagent will be dispensed into a reagent well.

Oftentimes it is desirable to leave the sample tray on the table top for an extended period of time so that a plurality of tests can be performed on the blood samples, i.e., so that a number of transfer discs can be filled with sample and different reagents. However, evaporation of sample occurs and such evaporation affects the concentration of sample in the sample cups. Changes in concentration will affect the particular chemical analysis being made of the sample. Accordingly, it is desirable to provide some means for preventing evaporation.

As will be described in greater detail hereinafter the cover of the present invention solves this problem of evaporation by providing a simple cover for the rotatable sample tray which can easily and simply be placed over the sample tray to prevent evaporation of samples from sample cups which are not at the sample pickup station and which has means thereon to maintain the cover in a stationary position when the sample tray is rotated.

SUMMARY OF THE INVENTION

According to the invention there is provided an evaporation reducing cover for a rotatable sample tray which has sample receiving receptacles therein and which is positioned on a supporting means, said cover being adapted to be loosely positioned over the sample tray without securement to the tray or the supporting means and with the underside thereof resting on and covering the open tops of the receptacles, having means for holding the cover in a stationary position when the sample tray is rotated including means for frictionally engaging the rotatable sample tray when it is rotated so that concentric alignment of said cover and the sample tray is maintained during rotation of the sample tray and having passage means therethrough for allowing liquid sample to be inserted into or withdrawn from a receptacle when such receptacle is in registry with said passage means.

DESCRIPTION OF THE PREFERRED EMBODIMENT

Figure 1:
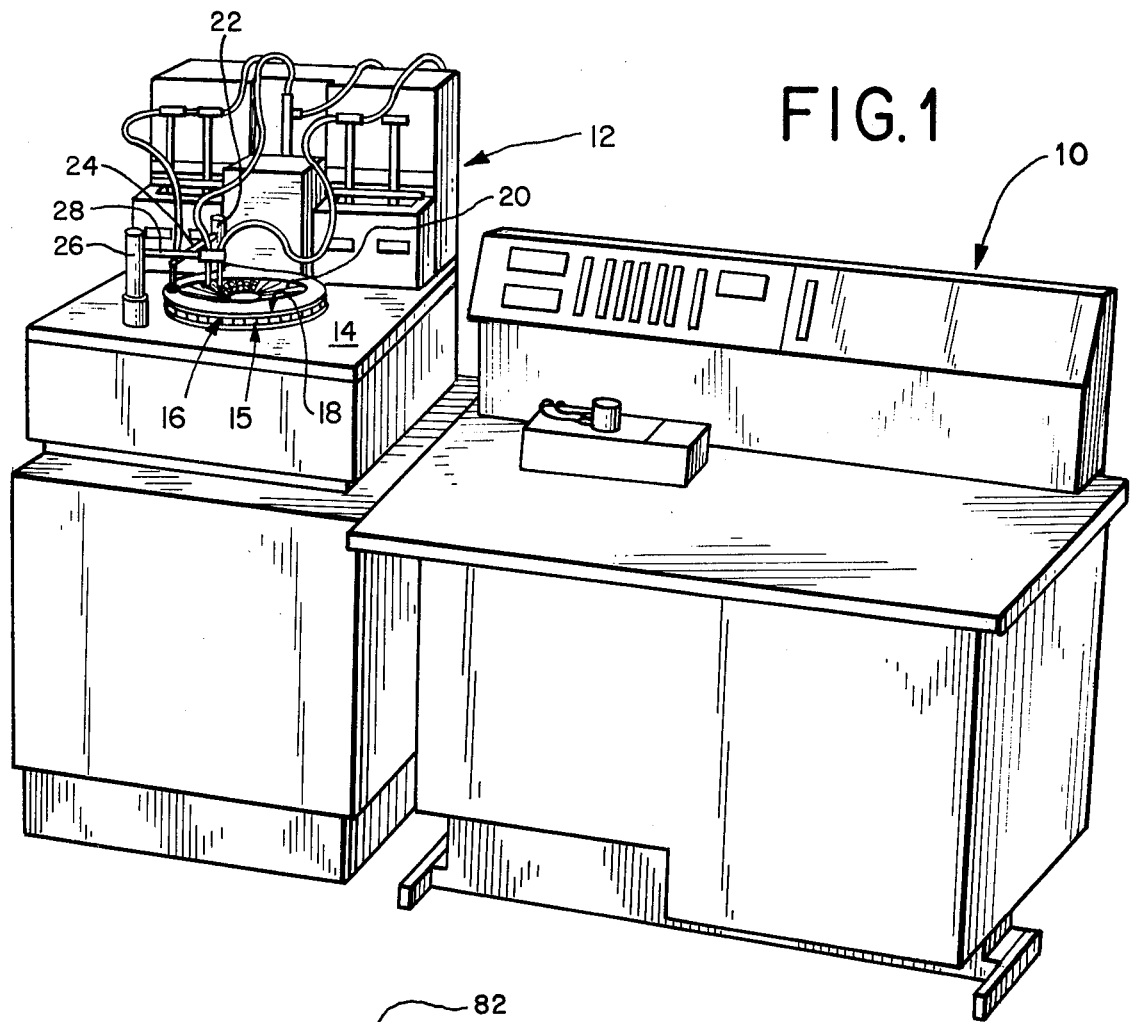
FIG. 1 is a perspective view of an automatic sample and reagent transfer and dispensing device having positioned on a table top thereof a rotatable sample tray and a cover therefor constructed in accordance with the teachings of the present invention and a perspective view of a centrifugal chemical analysis apparatus positioned adjacent the transfer and dispensing device.
Figure 2:
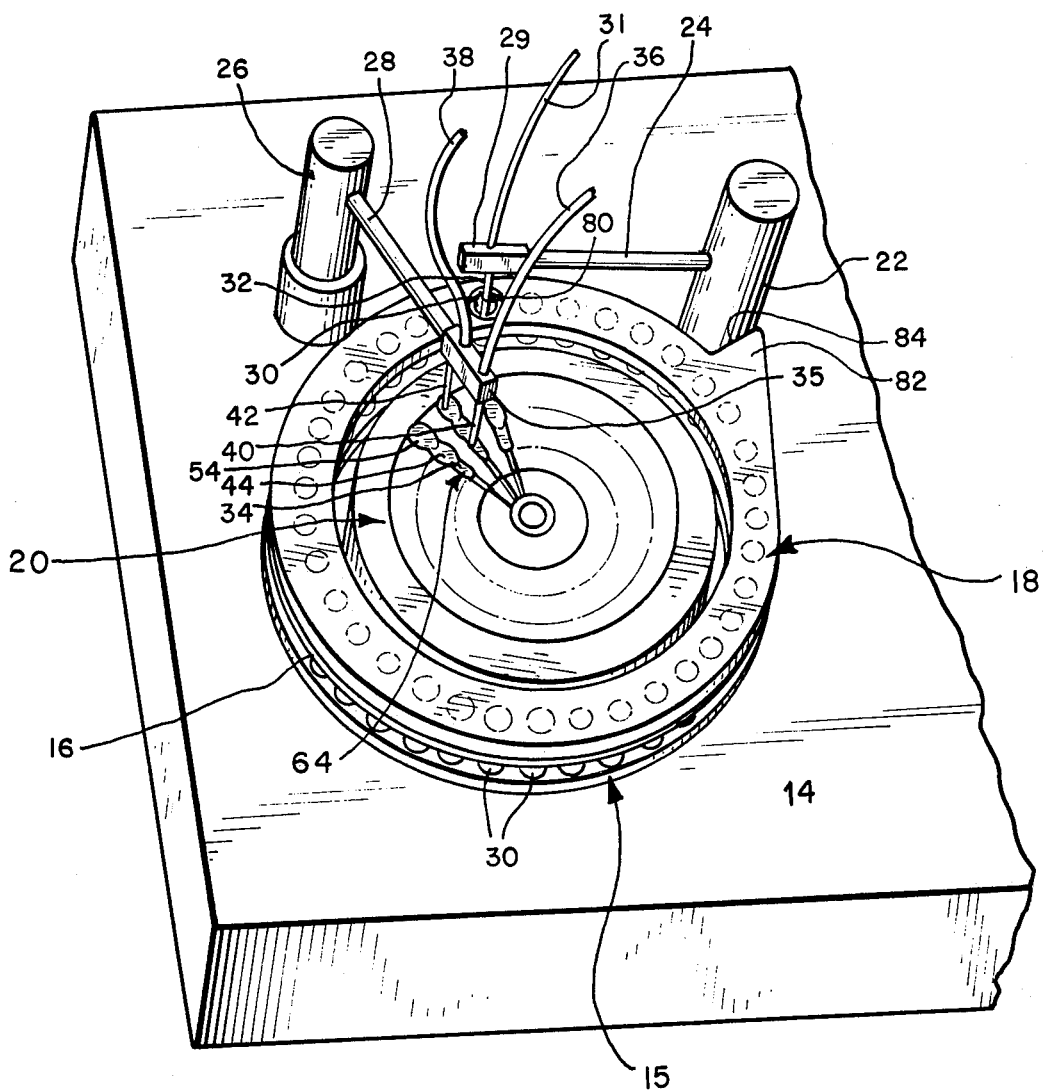
FIG. 2 is an enlarged top perspective view of the table top of the transfer and dispensing device shown in FIG. 1 with a transfer disc and the sample tray and cover therefor situated thereon.

Referring now to FIG. 1 there is illustrated therein a centrifugal chemical analysis apparatus 10 which is of the type sold under the trademark ROTOCHEM IIa by American Instrument Company, a division of Baxter Travenol Laboratories, Inc., Silver Spring, Md. Situated adjacent the analysis apparatus 10 is an automatic sample and reagent transfer and dispensing device 12 having an upper table top 14 on which is mounted a turntable 15 (FIG. 2). The device 12 is of the type sold under the trademark ROTOFILL by American Instrument Company, a division of Baxter Travenol Laboratories, Inc., Silver Spring, Md. Positioned on the turntable is an annular rotatable sample tray 16 on which is disposed a cover 18 constructed in accordance with the teachings of the present invention. Also positioned on the turntable within the circular space defined by the sample tray 16 is a rotatable transfer disc 20. As shown the automatic sample and reagent transfer and dispensing device 12 includes a first post 22 mounted on the table top surface 14 and having an arm 24 extending therefrom and a second post 26 also mounted on the table top 14 and having an arm 28 extending therefrom.

Referring now to FIG. 2, which is an enlarged perspective view of the table top 14 with the sample tray 16, transfer disc 20 and posts 22 and 26 thereon, it will be apparent that the first post 22 mounts the arm 24 so as to position the outer distal end 29 thereof over a sample cup 30 received in the sample tray 16 and forming a sample receiving receptacle therein. A tubing 31 extends to the outer end 29 of the arm 24 and is connected to an aspirating dip tube 32 depending from the distal end 29 of the arm 24. The position of the aspirating dip tube 32 defines a sample pickup station. In this position, the post 22 is lowered to lower the dip tube 32 into a sample cup 30 so that the dip tube 32 can aspirate a given amount of sample from the sample cup 30. Then the post 22 is raised and the arm 24 is rotated to a position over the transfer disc 20 and over a sample receiving well or chamber 34 where it is lowered for the dispensing of the given amount of sample into the well 34.

As shown in FIG. 2 the second post 26 mounts the arm 28 which has a distal end 35 adapted to mount one to three tubings thereon. In the illustrated embodiment two tubings 36 and 38 are shown extending to the end 35 of the arm 28 and are connected to respective dip tubes 40 and 42. Suitable mechanisms are provided for moving the arm 28 radially inwardly or outwardly so as to position one of the dip tubes such as dip tube 40 above a reagent receiving well or chamber 44 in the transfer disc 20 where a selected precise quantity of reagent can be mounted to the end 35 of the arm 28 for dispensing another reagent or water into the sample 34 or reagent well 44.

The transfer disc 20 also has a mixing well or chamber 54 therein which is located radially outwardly from the reagent well 44. The wells 34, 44 and 54 define a sample and reagent receiving and mixing channel 64 and a plurality of such channels 64 having the chambers therein are disposed in a spoke-like array on the transfer disc 20, each channel 64 extending along a radius from the center of the transfer disc 20.

Figure 3:
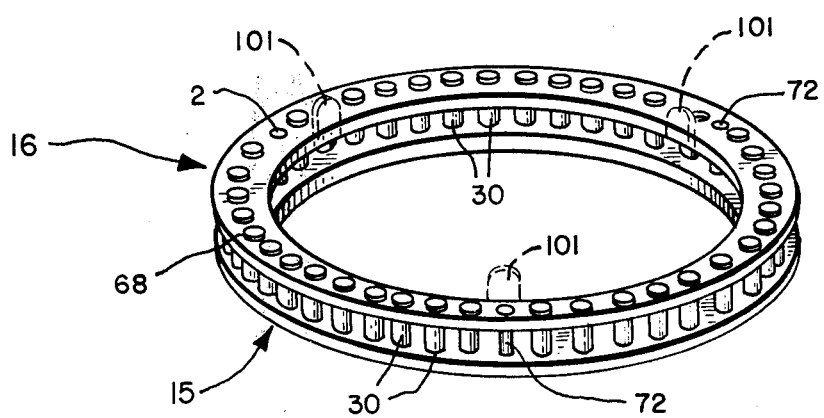
FIG. 3 is a perspective view of the sample tray.

Referring to FIG. 3, there is illustrated therein the sample tray 16 which includes a plate-like ring 68 in which a plurality of the sample cups 30 are received through openings in the ring 68. The bottoms of the sample cups 30 rest on the turntable 15. The ring 68 and the sample cups 30 are supported on the turntable 15 by a plurality, e.g., three, supporting and spacing posts 72.

The apparatus 10 and the device 12 as well as the portions thereof described above are all conventional and form no part of the present invention.

In the use of the apparatus 10 and the device 12 samples are first taken from patients and inserted into respective ones of the sample cups 30 which are then identified and positioned in the sample tray 16. Then the sample tray 16 is positioned on the turntable 15 on the tabletop 14 and a transfer disc 20 is positioned on the turntable 15 within the circular space defined by sample tray 16. Then the transfer and dispensing device 12 is operated to aspirate a given amount of sample from a sample cup 30 located at the sample pickup station defined by the position of the dip tube 32 and then to dispense that given amount of sample into one of the sample receiving wells 34 in one of the channels 64 in the transfer disc 20. Also, at the same time, a predetermined amount of a selected reagent is dispensed into one of the reagent receiving wells 44 in one of the channels 64. After this has been accomplished the turntable is indexed to rotate the sample tray 16 to position another sample cup 30 at the sample pickup station defined by the position of the dip tube 32 to repeat the aspiration, transfer and dispensing operation described above. This procedure is repeated automatically until a desired number of channels 64 have been filled with sample and reagent in the respective sample well 34 and reagent well 44 thereof. Then the arms 28 and 24 are moved horizontally away from the turntable so that the transfer disc 20 can be removed from the device 12 and placed in the apparatus 10 for centrifuging the sample from the well 34 over a wall in the channel 64 into the reagent well 44 and then sample and reagent are centrifuged over another wall in the chamber 64 into the mixing chamber 54.

Although not shown, it is to be understood that there is a radial passageway from each mixing chamber 54 to the outside of the transfer disc 20 and each of these radial passageways is adapted to be aligned with a reaction cuvette in a centrifuge device within the centrifugal chemical analysing apparatus. Each of the reaction cuvettes is fixed relative to the position of the adjacent mixing well 54 during rotation of the centrifuge device in which the transfer disc 20 is mounted. Then, during centrifugation, the mixed sample and reagent passes through the passageway in the transfer disc and through an opening in the reaction cuvette into the cuvette. The reaction cuvette has a light transmitting portion and upon each rotation of the centrifuge device, each cuvette is passed by a light source and a photosensor, the light source being positioned to pass light through the reaction cuvette and the photosensor being arranged to pick up light that is passed through the reaction cuvette. In this way, each time a reaction cuvette passes the light source, the reaction can be sensed, i.e., the optical density or light transmission of the reaction is sensed, and then by comparing the different sensings over a period of time a determination can be made of the rate of the reaction.

Inasmuch as it may be desired to make a number of different chemicaly analyses of the blood samples obtained from a number of patients, oftentimes the sample tray 16 is left on the turntable for an extended period of time for supplying samples to a number of transfer discs which are utilized in performing different chemical analyses of the blood sample utilizing the centrifugal chemical analysis apparatus 10. Thus, although it only takes about four minutes to completely fill a transfer disc 20, there are times when the sample tray may be allowed to rema.n on the turntable for a period of four hours or more while different chemical analyses are being made with the chemical analysis apparatus 10 since each chemical analysis may take at least ten minutes to complete.

When the sample cups 30 are allowed to remain in the sample tray 16 for such an extended period of time, evaporation of the sample occurs and the concentration of the sample, e.g., blood plasma, is changed. Such changes in concentration adversely effect the accuracy of the chemical analysis of the sample. Accordingly, it is desirable to have some means for covering the sample cups 30 in the sample tray 16 to prevent evaporation of the sample. According to the teachings of the present invention, evaporation of the sample in the sample cups 30 is minimized, if not altogether prevented, by the provision of the cover 18.

Figure 4:
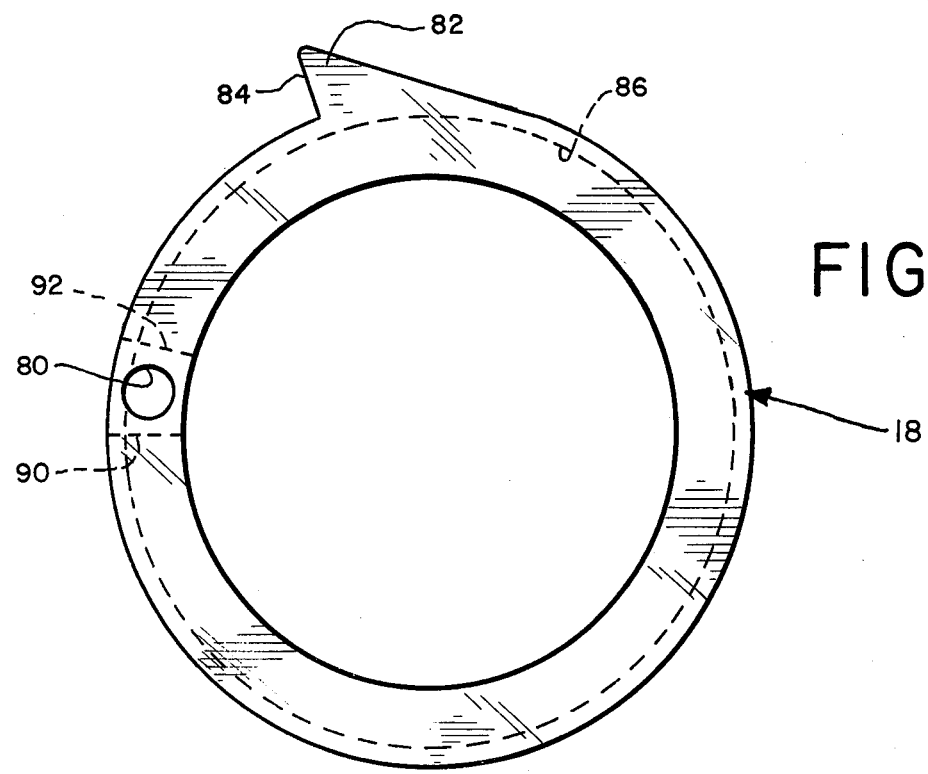
FIG. 4 is a top plan view of the cover of the present invention.

Referring now to FIGS. 2, 3 and 4, the cover 18 has a generally annular or ring shape and is made from a sheet of planar transparent plastic material. Alternatively, the cover 18 can be a molded part, can be translucent or opaque and/or can be made of another material such as a metal. In one realization of the present invention, the cover 18 was made from a ¼ inch thick piece of clear plexiglass and had an outer diameter of approximately 8⅞ inches and an inner diameter of 6¾ inches, i.e., an annular area sufficient to cover the ring 68 of the sample tray 16 and more particularly to cover the tops of the sample cups 30 received in the sample tray 16.

The cover 18 also has passage means therethrough, which in a preferred embodiment, is realized by a circular opening 80. As will be explained in greater detail hereinafter, the circular opening 80 is adapted to be positioned at the sample pickup station beneath the dip tube 30.

Inasmuch as the sample tray 16 is rotated each time the turntable is indexed to place another sample cup 30 at the sample pickup station, the cover 18 is provided with means for holding the cover 18 in a stationary position over the sample tray 16. Such holding means are realized in part by a projection 82 extending horizontally and radially outwardly from the annular planar cover 18. As shown, the projection 82 has a shoulder 84 which is adapted to engage and abut against the first post 22. Also it will be noted that the circular opening 80 is located a predetermined angular distance from the projection 82 in order to properly locate the opening 80 relative to the post 22 and in a desired location at the sample pickup station. The engagement of the projection 82 with the post 22 prevents rotation of the cover 18.

Figure 5:
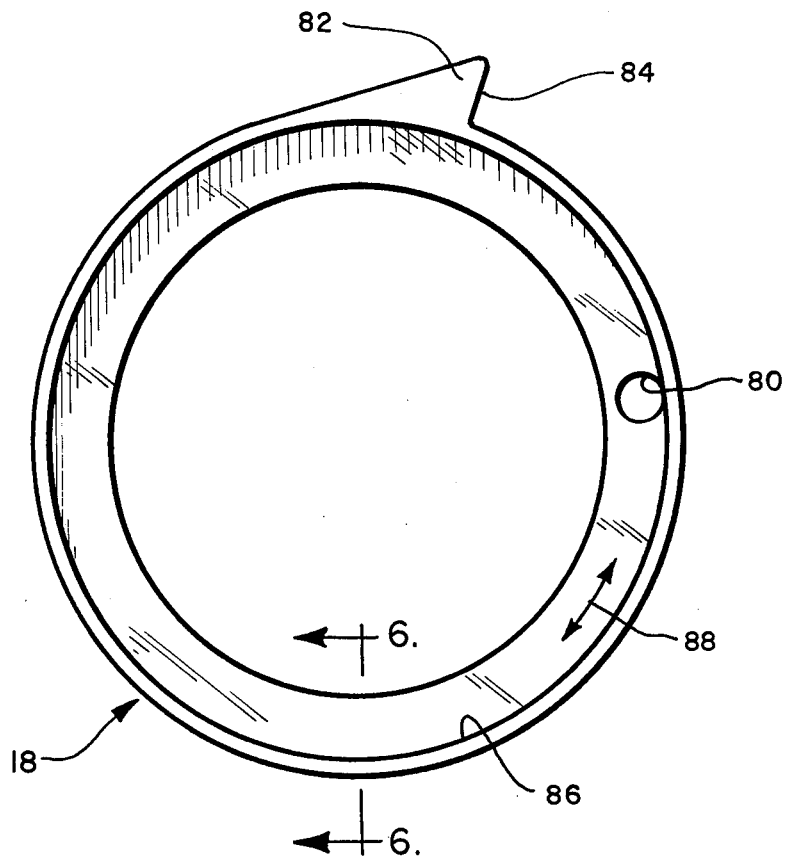
FIG. 5 is a bottom plan view of the cover of the present invention.
Figure 6:
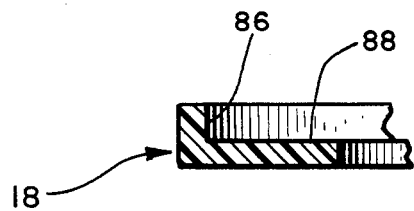
FIG. 6 is a sectional view of the cover taken along line 6—6 of FIG. 5.

The means for holding the cover 18 in a stationary position is also realized by an annular shoulder 86 on the underside of the planar annular cover 18 as best shown in FIGS. 5 and 6. The diameter of the annular shoulder 86 is slightly greater than the diameter of a circular envelope defined by the radially outwardly disposed top side edge of the sample cups 30 in the sample tray 16.

In use, the annular planar cover 18 can be easily positioned by hand over the sample tray 16 with the tops of the sample cups 30 received within a recess 88 defined beneath the cover 18 and inwardly of the annular shoulder 86 and with the shoulder 84 of the projection 82 abutting against the post 22. With the cover 18 in that position, the circular opening 80 will be in registry with the open top of one of the sample cups 30 at the pickup station so that the dip tube 32 can be inserted into that sample cup 30 for withdrawing a predetermined amount of sample therefrom.

With the cover 18 constructed in the manner described above the tops of the sample cups 30 are allowed to travel within the recess 88 when the turntable is indexed to rotate another sample cup 30 to the sample pickup station. The engagement of the shoulder 84 on the projection 82 with the post 22 prevents rotation of the cover 18 and the frictional engagement between radially outwardly disposed top side edges of the sample cups 30 with the annular shoulder 86 prevents horizontal movement of the cover 18 as the tops of the sample cups 30 frictionally engage the underside of the cover in the recess 88 and exert a moment force on the cover 18 when the sample tray 16 is rotated.

It will be understood of course that other means can be provided for maintaining the cover 18 in a stationary position over the sample tray 16. For example, another post can be provided on the table top 14, 180 degrees opposite the post 22 and another projection can be provided on the cover 18 diametrically opposite the projection 82, so that any torque or moment forces exerted on the cover 18 by the tops of the sample cups frictionally and slidingly engaging the undersurface of the cover 18 will act on the posts to prevent the cover 18 from being moved horizontally off of the sample tray 16. Alternatively, the inner edge of the cover 18 can be configured to engage the transfer disc 20 to maintain the cover 18 stationary over the sample tray 16. As a further alternative, a swing arm supported on the table top 14 of the device 12 can be provided and connected at its outer end to the cover 18, such that the cover 18 can be swung horizontally to and from a position over the sample tray 16.

Still another alternative means, and another preferred means, for holding and maintaining the cover 18 in a stationary position over the sample tray 16 is a bearing engagement between the inner circular edge of the cover 18 and upstanding tabs or an upstanding lip or rim on the inner edge of the ring 68 of the sample tray 16. Several such tabs are shown in phantom in FIG. 3 and identified by reference numeral 101. When upstanding tabs 101 or an upstanding rim are (is) provided on the ring 68 for locating and maintaining the cover 18 in a stationary position, the underside of the cover 18 can be flat without the shoulder 86.

Moreover, instead of a circular opening 80, the cover 18 can have a radial slot therein defined between two radially extending edges 90 and 92 in the cover 18 shown in phantom lines in FIG. 4. When a radial slot is utilized the edge 90 of the slot is bevelled on the underside of the cover 18 to facilitate movement of the tops of the sample cups 30 underneath the cover 18 at the edge 90.

From the foregoing description of the preferred embodiment of the cover 18 of the present invention it will be apparent that the cover 18 has a number of advantages some of which have been described above and others of which are inherent in the invention. In particular, the cover 18 is of simple configuration and design and is configured as described above, not only for covering sample cups 30 in the sample tray 16 which are not positioned at the sample station but also configured with the projection 82 and the annular shoulder 86 which cooperate to maintain the cover 18 in a stationary position over the sample cups 30 in the sample tray 16 when the sample tray 16 is rotated.

Further from the foregoing description it will be apparent that obvious modifications and variations can be made to the cover 18 of the present invention without departing from the teachings of the present invention. Accordingly, the scope of the invention is only to be limited as necessitated by the accompanying claims.

We claim:

1. An evaporation reducing cover for a rotatable sample tray which has sample receiving receptacles therein and which is positioned on a supporting means, said cover being adapted to be loosely positioned over the sample tray without securement to the tray or the supporting means and with the underside thereof resting on and covering the open tops of the receptacles, having means for holding the cover in a stationary position when the sample tray is rotated including means for frictionally engaging the rotatable sample tray when it is rotated so that concentric alignment of said cover and the sample tray is maintained during rotation of the sample tray and having passage means therethrough for allowing liquid sample to be inserted into or withdrawn from a receptacle when such receptacle is in registry with said passage means.

2. The cover according to claim 1 being generally planar.

3. The cover according to claim 1 having a generally planar ring shape.

4. The cover according to claim 1 being transparent.

5. The cover according to claim 1 having a generally annular configuration.

6. The cover according to claim 5 being transparent.

7. The cover according to claim 5 being generally planar.

8. The cover according to claim 7 wherein said holding means comprises at least one projection which extends generally horizontally, radially outwardly from said cover for engaging an abutment on a table supporting the sample tray.

9. The cover according to claim 8 wherein said means for frictionally engaging said sample tray comprises an annular shoulder on the underside of said annular planar cover, said annular shoulder being sized to fit around a circular envelope defined by the radially outwardly disposed top side edges of the tops of the receptacles in the sample tray, which receptacles are defined by sample cups received in the sample tray, and sized to engage the top side edges of the sample cups to prevent horizontal movement of said cover as said tops of the sample cups frictionally engage the underside of said cover and exert a moment force on said cover when the sample tray is rotated thereby to define and form said means for frictionally engaging said sample tray.

10. The cover according to claim 7 wherein said passage means is defined by an opening through said annular planar cover.

11. The cover according to claim 7 wherein said passage means is defined by a horizontally radially extending slot through said annular planar cover.

12. The cover according to claim 8 wherein said means for frictionally engaging said sample tray comprises an inner circular edge of said cover which is adapted for bearing engagement with upstanding means extending upwardly from the sample tray.

13. The cover according to claim 1 having an annular shoulder on the underside thereof positioned on the outer side of the circular array of receptacle tops on the sample tray.

14. The cover according to claim 5 wherein said means for frictionally engaging said sample tray comprises an inner circular edge of said cover which is adapted for bearing engagement with upstanding means extending upwardly from the sample tray.

* * * * *